(12) United States Patent
Lowik et al.

(10) Patent No.: US 6,998,272 B2
(45) Date of Patent: Feb. 14, 2006

(54) MACROCYCLIC COMPOUNDS AND THEIR USE

(75) Inventors: Dennis Lowik, Cambridge (GB); Christopher Robin Lowe, Cambridge (GB)

(73) Assignee: Prometic Biosciences, Ltd., (GB)

( * ) Notice: Subject to any disclaimer, the term of this patent is extended or adjusted under 35 U.S.C. 154(b) by 361 days.

(21) Appl. No.: 10/149,508

(22) PCT Filed: Dec. 11, 2000

(86) PCT No.: PCT/GB00/04725

§ 371 (c)(1),
(2), (4) Date: Oct. 28, 2002

(87) PCT Pub. No.: WO01/42228

PCT Pub. Date: Jun. 14, 2001

(65) Prior Publication Data

US 2004/0115724 A1    Jun. 17, 2004

(30) Foreign Application Priority Data

Dec. 10, 1999  (GB) ................................. 9929318

(51) Int. Cl.
*G01N 33/566* (2006.01)
*C07D 403/00* (2006.01)

(52) U.S. Cl. ...................... 436/501; 544/212; 544/359
(58) Field of Classification Search ................ 544/212, 544/359; 436/501
See application file for complete search history.

(56) References Cited

U.S. PATENT DOCUMENTS

| 5,199,959 | A |   | 4/1993 | Sung et al. |
| 5,219,955 | A |   | 6/1993 | Sung et al. |
| 5,344,931 | A | * | 9/1994 | Cipolli et al. ............... 544/195 |
| 5,493,022 | A |   | 2/1996 | Kaul et al. |

FOREIGN PATENT DOCUMENTS

| EP | 0 560 567 A1 | 9/1993 |
| WO | WO 91/04987 A1 | 4/1991 |

OTHER PUBLICATIONS

Anelli, P.L. et al. "Doubly and Triply Bridged Polyoxapolyazaheterphanes Derived from 2,4,6-Trichloro-s-triazine" *J. Org. Chem.* (1984), 49:4197-4203; XP-000615835.

Graubaum, H. et al. "Synthese und Transportuntersuchungen von Dioxapolyazacalix[4]arenen und Triazino-Kronenethem" *J. Prakt. Chem.* (1998), 340: 165-170; XP-000995728.

Ishida, H. et al. "Serine Proteinases Mimics: Hydrolytic Activity of Cyclic Peptides Which Include a Non-natural Amino Acid" *Tetrahedron Lett.* (1995), 36(49):8987-8990; XP-002165633; Elsevier Science Ltd., Great Britain.

Lipkowski, P. et al. "Self-assembly of a [2×2] hydrogen bonded grind" *Chem. Commun.* (1999), pp. 1311-1312; XP-002165632.

Mathias, J. et al. "Self-Assembly through Hydrogen Bonding: Peripheral Crowding—A New Strategy for the Preparation of Stable Supramolecular Aggregates Based on Parallel, Connected $CA_3.M_3$ Rosettes" *J. Am. Chem. Soc.* (1994), 116:4326-4340; XP000942081; American Chemical Society.

Mascal, M. et al. "Synthesis and Structural Characterization of an S-linked Calix[3]azine" *Tetrahedron Lett.* (1997), 38(43):7639-7640; Elsevier Science Ltd., Great Britain.

Rasmussen, P.H. and Rebek, Jr., J. "A Pseudopeptide Platform with Side Chains Addressable for Combinatorial Applications" *Tetrahedron Lett.* (1990), 40:3511-3514; XP-002165631; Elsevier Science Ltd., Great Britain.

Shu, C.-M. and Chung, W.-S. "Synthesis of Calix[4]arenes with Four Different 'Lower Rim' Substituents" *J. Org. Chem.* (1999), 64:2673-2679; XP-002165630; American Chemical Society.

* cited by examiner

*Primary Examiner*—Long V. Le
*Assistant Examiner*—Shafiqul Haq
(74) *Attorney, Agent, or Firm*—Saliwanchik, Lloyd & Saliwanchik (57) ABSTRACT

The subject invention pertains to macrocyclic compounds, and their use, the compounds having the formula (I)

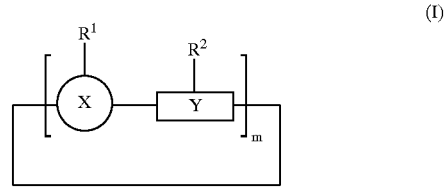

wherein X is a ring bearing an optionally-protected functional group or solid phase group $R^1$, Y is a linker optionally bearing an optionally-protected functional group or solid phase group $R^2$, m is at least 3, and each instance of X, Y, $R^1$ and $R^2$ may be the same or different.

8 Claims, 8 Drawing Sheets

MACROCYCLIC COMPOUNDS AND THEIR USE

FIELD OF THE INVENTION

The invention relates to macrocylic compounds and their use.

BACKGROUND OF THE INVENTION

There is a growing interest in macrocyclic molecules that may be used as scaffolds in the combinatorial synthesis of receptor molecules. Many macrocyclic molecules have been synthesised. However, in many cases, their synthesis is difficult and/or relatively inflexible towards functionalisation. For some recent examples of unsymmetrically substituted macrocycles, see Rasmussen et al, J. Tet. Lett. (1999) 40: 3511; Höbger et al., Chem. Eur. J. (1999)5:1686; Shu et al, J. Org. Chem. (1999) 64: 2673; and Cho et al, Bioorg. Med. Chem. (1999)7: 1171. Cho et al discloses cyclic and linear oligocarbamates. Only in the case of cyclic peptides have stepwise synthesis, facile functionalisation of the building blocks, and solid phase synthesis been reported.

Some known macromolecules are based on triazine. Oligomers and cyclic molecules of this type are disclosed by Lipkowski et al, Chem. Commun. (1999) 1311; Ichihara et al, Chem. Letters (1995) 631; Mathias et al, J. Am. Chem. Soc. (B1994) 116: 4326; and Anelli et al, J. Org. Chem. (1984), 49: 4197. In particular, Mathias et al discloses linear triazine-based macromolecules, capable of supramolecular aggregation. Ichihara et al discloses triazine-linked porphyrins. Lipkowski et al discloses compounds that form a [2×2] hydrogen-bonded grid.

Known macrocycles include those of the formula where X is a ring which may bear a group $R^1$, Y is a linker which optionally bears a group $R^2$, and m is an integer. Thus, Rasmussen et al discloses compounds in which X is a benzene ring, $R^1$ is H, Y is peptidic, $R^2$ is a functional group, and m is 3, for combinatorial applications. Anelli et al discloses compounds in which X is triazine, $R^1$ is Cl and m is 2, as intermediates to triply-bridged derivatives, capable of molecular recognition and of use as phase-transfer catalysts.

SUMMARY OF THE INVENTION

The present invention is based on a stepwise approach to the combinatorial synthesis of macromolecules having a desired/defined stereochemistry and also functional groups effectively predefined both for the potential uses of the molecule and for its synthesis (which can be done on a solid phase).

According to a first aspect of the present invention, compounds are of the formula given above, wherein X is a ring bearing an optionally-protected functional group $R^1$, Y is a linker optionally bearing an optionally-protected functional or solid phase group $R^2$, and m is at least 3; each of X, Y, $R^1$ and $R^2$ may be the same or different.

Compounds of this invention provide, typically by choice of the functional group $R^1$, an effective recognition element. Depending on the choice of groups $R^1$, compounds of the invention have a variety of uses, for example depending on their binding properties, for diagnostics and therapeutics. They may be used for affinity binding, phase-transfer agents and ionophors. Compounds of the invention may also be used for molecular imprinting and for other purposes such as removing pesticides from water and for high performance chromatography. In a particular example, compounds of the invention may be constructed to recognise portions of proteins, and thereby have value for targeting or separation purposes. Their utility may also depend on characteristics of the molecule other than $R^1$, e.g. the value of m (which determines the "hole" in which foreign molecules may be bound). The characteristics of compounds of the invention may be extended by using them in a multi-layer format.

DESCRIPTION OF THE INVENTION

X is preferably triazine. It may also be any ring that bears or can readily be reacted to form the three given substituents on X, i.e. $R^1$ and two linkers Y. Y may be any suitable linker, of any desired length; it will often be preferred that the molecule forming the linker terminates in a functional groups such as NH, which can readily be reacted with a carbon atom in the ring X. By this means of synthesis, any group $R^1$ or $R^2$ may already be present on X/Y. This allows a wide selection of suitable functional groups, according to the desired end purpose. Suitable protecting groups, their introduction and removal, are well known to those in the art, and will be used as necessary for protection during synthesis. The primary purpose of the functional group $R^1$ will be with respect to foreign molecules to be bound by macrocycles of the invention; for this purpose, the groups $R^1$ may be the same or different. $R^1$ may also be used as a point of attachment to a solid phase. $R^2$ may be absent; if present, it will generally be chosen with a view to ready immobilisation of the linker, to facilitate synthesis and/or use of the macrocycles. As indicated below, this invention allows effective solid phase chemistry to be used.

m will typically be 3. It may however be a higher integer, e.g. 4, 5 or 6, depending on the desired size of the macrocycle.

The solid phase may be any material that may conveniently be used to separate macrocyclic compounds of the invention from solutes in a contacting solution. Examples of suitable solid phase support materials include, but are not limited to, polysaccharides such as agarose, cellulose, dextran, starch, alginate and carrageenan; synthetic polymers such as polystyrene, styrene-divinylbenzene copolymers, polymethacrylates, (e.g. poly(hydroxyethylmethacrylate), polyvinyl alcohol, polyamides, polyacrylamides and perfluorocarbons; inorganic materials such as glass, silica and metal oxides; and composite materials.

A variety of chemistries have been developed for the attachment of affinity ligands to solid phases. It will be appreciated by those skilled in the art that any convenient linker chemistry may be used as a means of attachment of macrocyclic compounds of the invention to a solid phase. Such linker chemistry may include both cleavable and non-cleavable groups. It will also be appreciated by those skilled in the art that macrocyclic ligands of the invention may be attached to a solid phase on completion of their synthesis or built up on the surface of a solid phase in step-wise fashion by solid phase synthesis. It will also be evident to those skilled in the art that libraries of macrocyclic compounds of the invention with differing X, Y, $R^1$ and $R^2$ groups may be constructed and subsequently screened for binding activity towards target compounds.

Macrocyclic compounds of the invention have general utility for the capture of complementary molecules. It will be appreciated that such compounds have many potential applications. Applications of compounds of the invention include, but are not limited to, the analysis, separation, isolation, purification, quantification, characterisation, or identification of chemical, biological or therapeutic compounds, the diagnosis of disease, and the treatment of disease. For example, compounds that can be separated from admixture with others include organic heterocycles such as cyanuric acid and saccharide-containing compounds such as octylglucosides. Examples of therapeutic application are in the treatment of immune disorders and metabolic disorders by capture or clearance of carbohydrates and glycoproteins, and the removal of toxic substances from blood.

For the purposes of illustration only, and with reference to Scheme 1, the invention will now be described with reference to the synthesis of macrocycles based on the triazine unit as a building block, with each unit comprising a triazine ring and a linker moiety (piperazine or diamine). In each stage of the synthesis, the chain can be either elongated or cyclised to the macrocycle of interest. The use of two orthogonal protective groups ($p^1$, $p^2$) on either side of the oligomers, allows control of the length of triazine-piperazine chain. In addition, it is possible to functionalise each triazine unit in the chain differently by reaction with particular amines. In Examples 1 and 2, piperazine was used as the linker, in order to create relatively rigid macrocycles. It will be evident to those skilled in the art that larger rings may be prepared and that other linkers may be used, thereby increasing the diversity even further.

The following Examples illustrate the invention. Reference may also be made to the accompanying Schemes 2 to 4.

EXAMPLE 1

Preparation of Macrocyclic Triazine Compounds in Solution

The synthesis of the basic macrocyclic structures commenced with mono-Boc protection of piperazine 1 using a modification of the procedure described by Carpino et al, J. Org. Chem (1983) 48:661. Reaction of monoprotected piperazine 2 with cyanuric chloride gave the monosubstituted product 3 in 93% yield, using the procedures of Koopman et al, J. Rec. Trav. Chim. Pays-Bas (1958) 77:235 and Beech, Chem. Soc. C. (1967) 466. Compound 3 can be used throughout the synthesis as a convenient building block for the elongation of triazine-piperazine oligomers. Mono-Z protected piperazine was chosen as the second substituent on the triazine 3, since it provided a second piperazine moiety, orthogonally protected. The mono-Z-protected piperazine was obtained by subsequent reaction of 2 with Z-chloride and TFA to give a quantitative yield of piperazine 5. This route is convenient and gives high yield. In addition, the reaction of piperazine with Z-chloride only gave the bisubstituted product.

The reaction of Z-protected compound 5 with 3 afforded bisubstituted triazine 6 in 85% yield. Finally, the third substituent (amylamine) was introduced by refluxing 6 with an excess of amylamine to give trisubstituted triazine 7a in 99% yield; see Li et al, J. Org. Chem. (1996) 61:1779. Diversity can be achieved by varying the amine in this step; other model amines used included benzylamine, cyclohexylamine, dodecylamine, 2-phenylethylamine and aniline, all of which gave trisubstituted products.

7b–d were obtained in 98%, 91% and 85% yield, respectively. These reactions show that a great variety of amines may be used in this reaction, to provide the desired diversity. The triazines 7 are also the starting point for the preparation of a series of functionalized triazine-piperazine oligomers that can be eventually cyclised. At this point, compound 7a was chosen to continue the work: either the Boc or the Z-group could be removed to functionalise further this compound. Thus, in order to obtain the precursor for the synthesis of a bis-triazine macrocycle, compound 7 was subjected to subsequent hydrogenolysis and a reaction with cyanuric chloride to afford dichloride 8 in a yield of 43%. Preliminary results revealed that higher yields of macrocycles could be obtained if the last protective group before cyclisation was a Boc group rather than a Z-group. Alternatively, compound 7 was treated with TFA, followed by a reaction with dichloride 3, using triethylamine as a base to give a quantitative yield of bis-triazine 9. The remaining chloride was then substituted using an excess of isobutylamine to afford compound 10 in 93% yield. Removal of the Z-group and reaction with cyanuric chloride gave dichloride 11 in 61% yield, as a precursor for the synthesis of a tris-triazine-piperazine macrocycle. Elongation of bis-triazine 10 was obtained by subsequent reaction with TFA and building block 3 to produce tris-triazine 12 in a yield of 93%. The remaining chlorine was displaced with cyclohexylamine to give tris-triazine 13 in 92% yield. Repetition of these steps also afforded the precursors for the tetra-, penta- and hexa-triazine-piperazine macrocycles 14, 17 and 20 in 62%, 46% and 43% overall yields, respectively, from compound 13.

Figure 1:
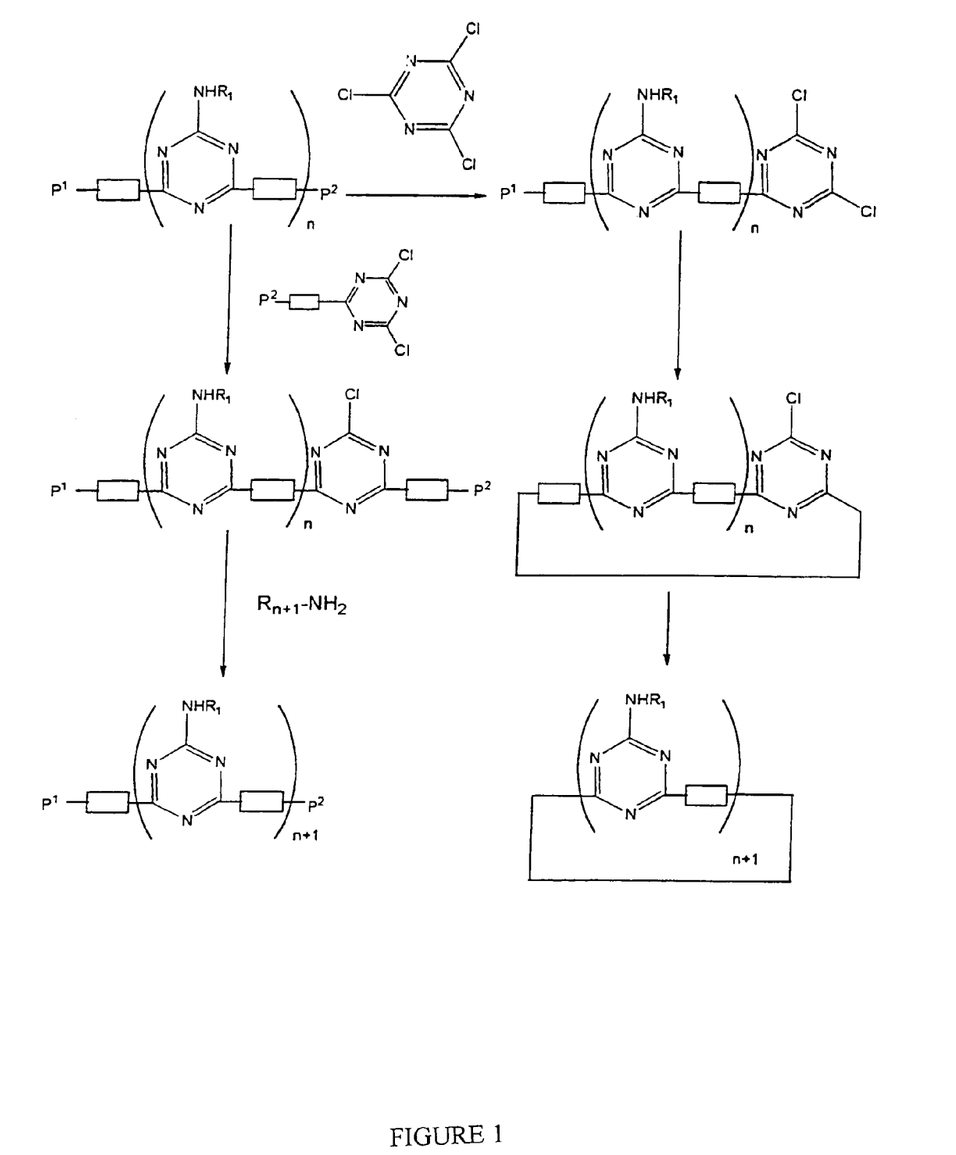
FIG. 1 shows a reaction scheme for preparing macrocyclic compounds of the present invention.
Figure 2:
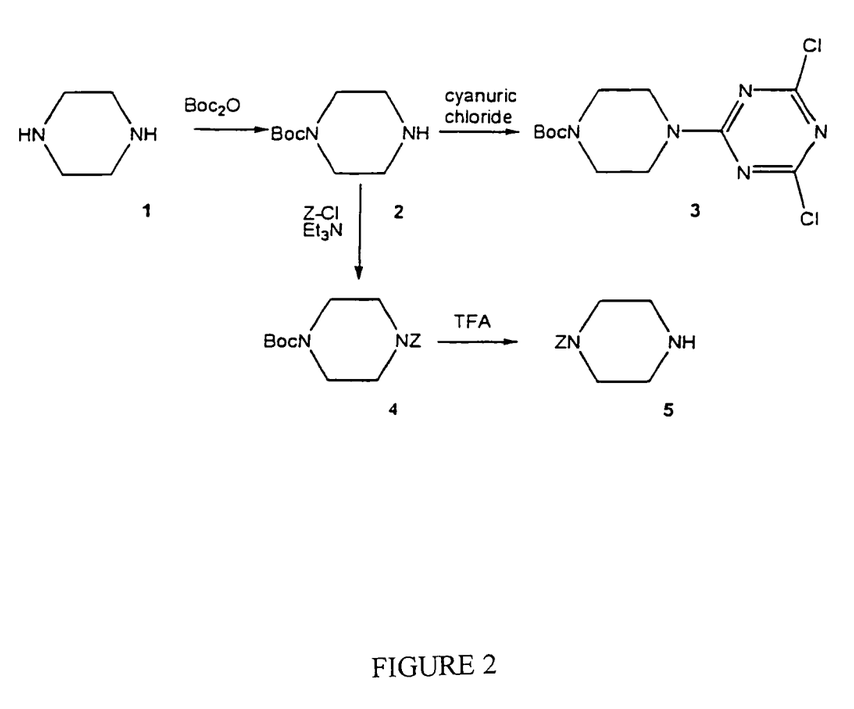
FIG. 2 shows a reaction scheme for preparing macrocyclic compounds of the present invention.
Figure 3A:
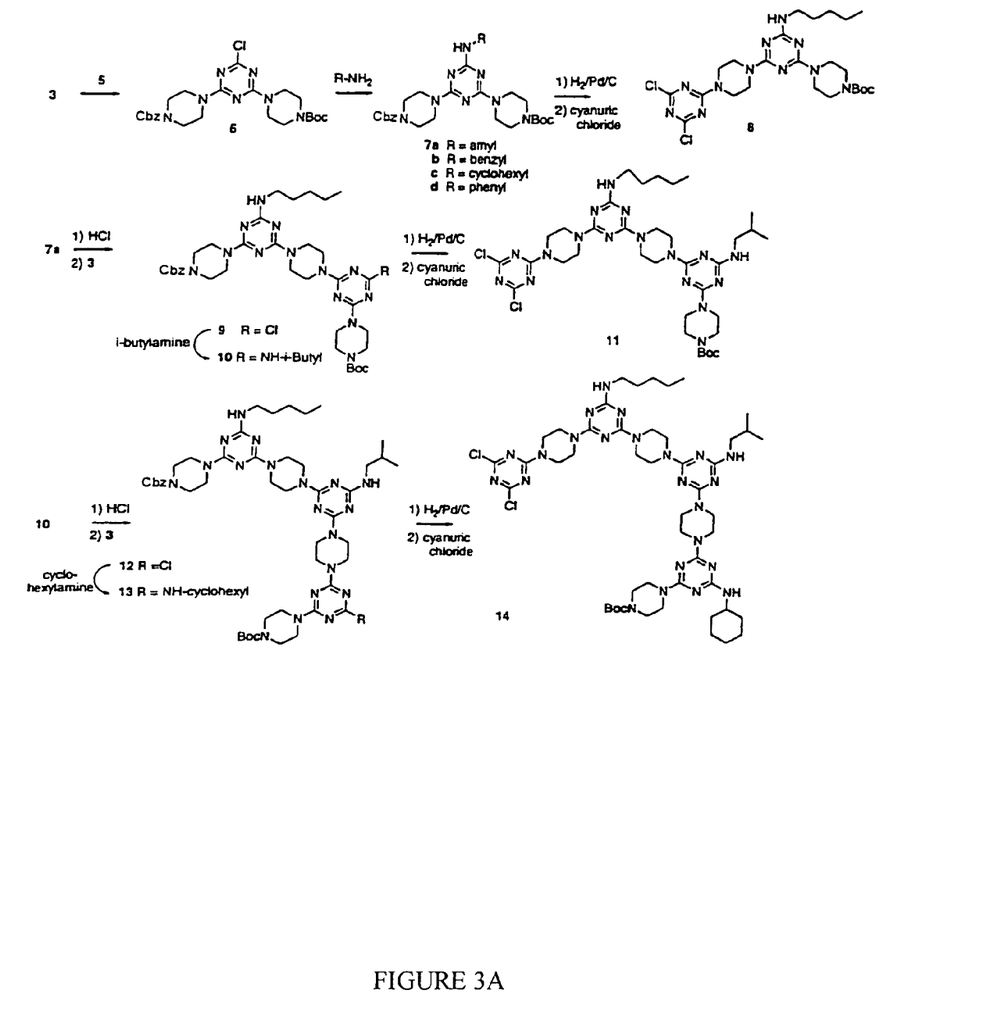
FIG. 3A and FIG. 3B shows a reaction scheme for preparing macrocyclic compounds of the present invention.
Figure 3B:
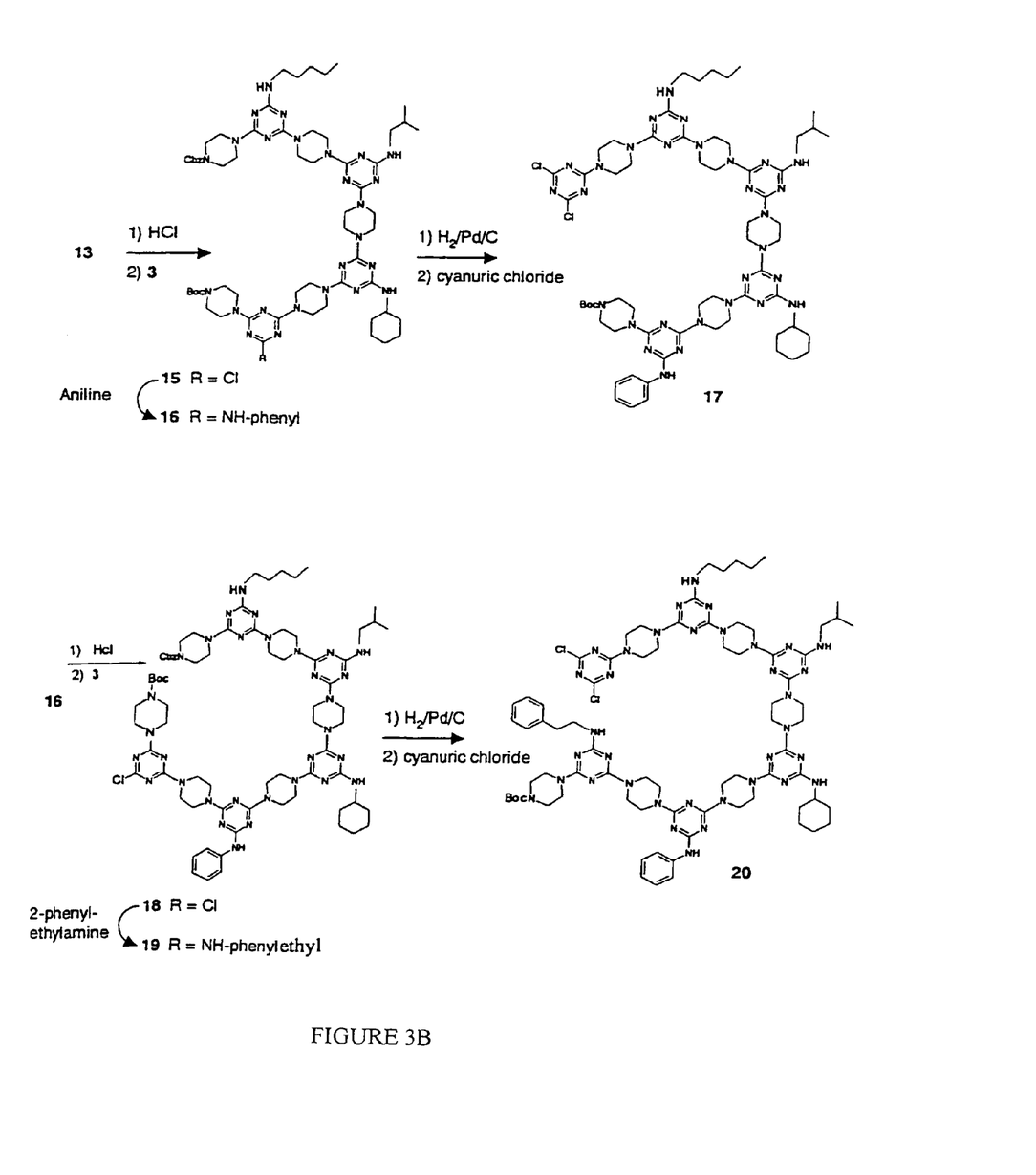
Figure 4:
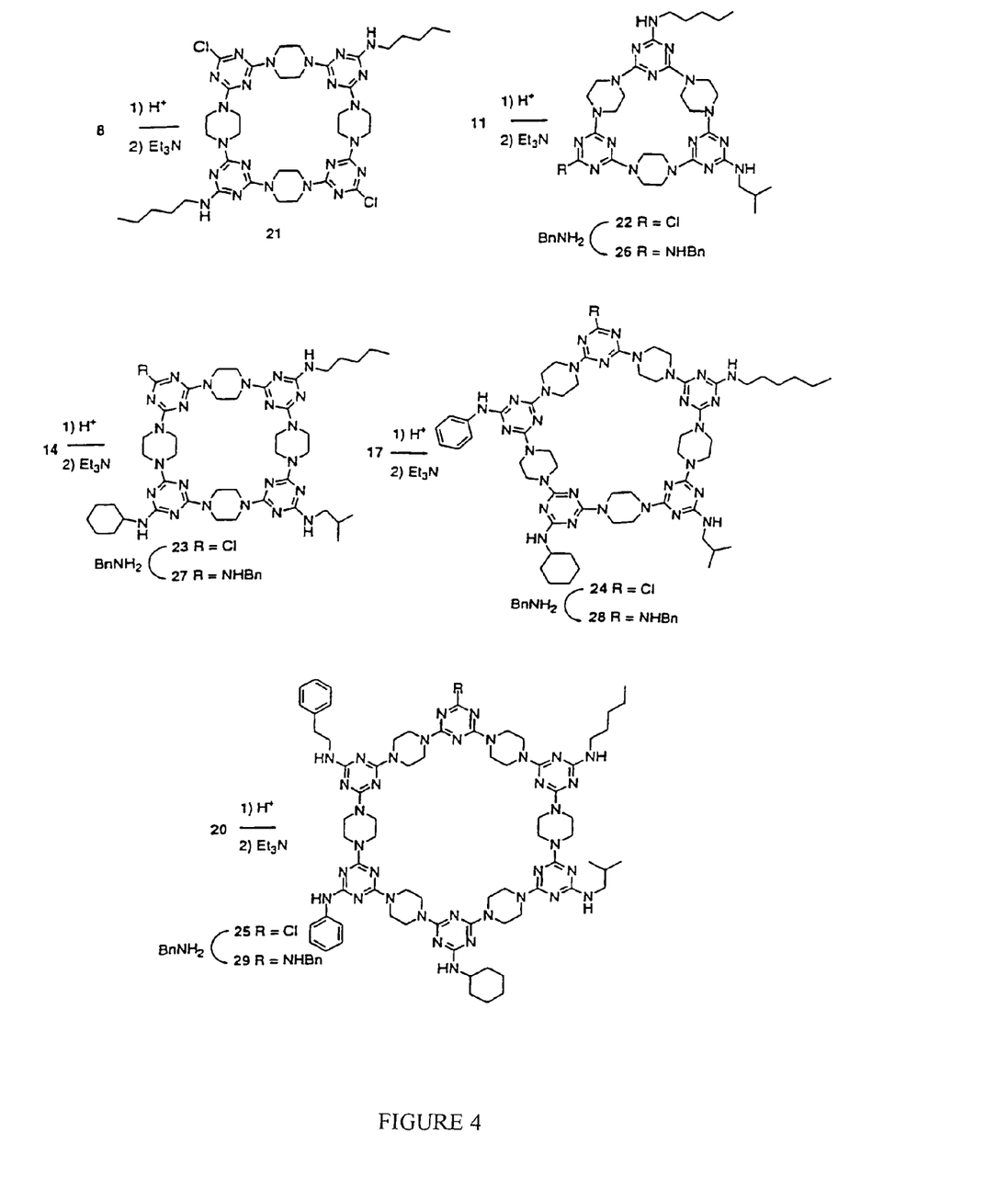
FIG. 4 shows a reaction scheme for preparing macrocyclic compounds of the present invention.

The triazine-piperazine oligomers 8, 11, 14, 17 and 20 were used to prepare their respective macrocycles by subsequent treatment with acid and base (FIG. 4). All compounds, except 8, could be converted to their corresponding macrocycles in fair yields (59–83%). Compound 8 produced only the dimer (tetra-triazine 21), while for the others, dimers were not obtained under the reaction conditions employed. Finally, the remaining chlorines in 22, 23, 24 and 25 were substituted using an excess of benzylamine to give 26, 27, 28 and 29.

EXAMPLE 2

Figure 5:
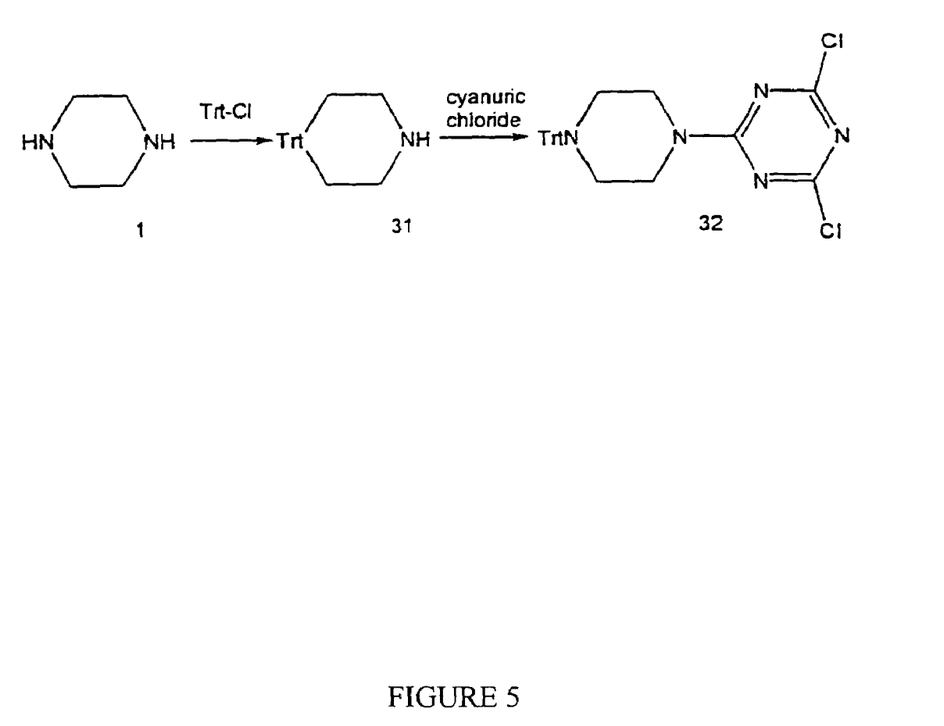
FIG. 5 shows a reaction scheme for preparing macrocyclic compounds of the present invention.
Figure 6:
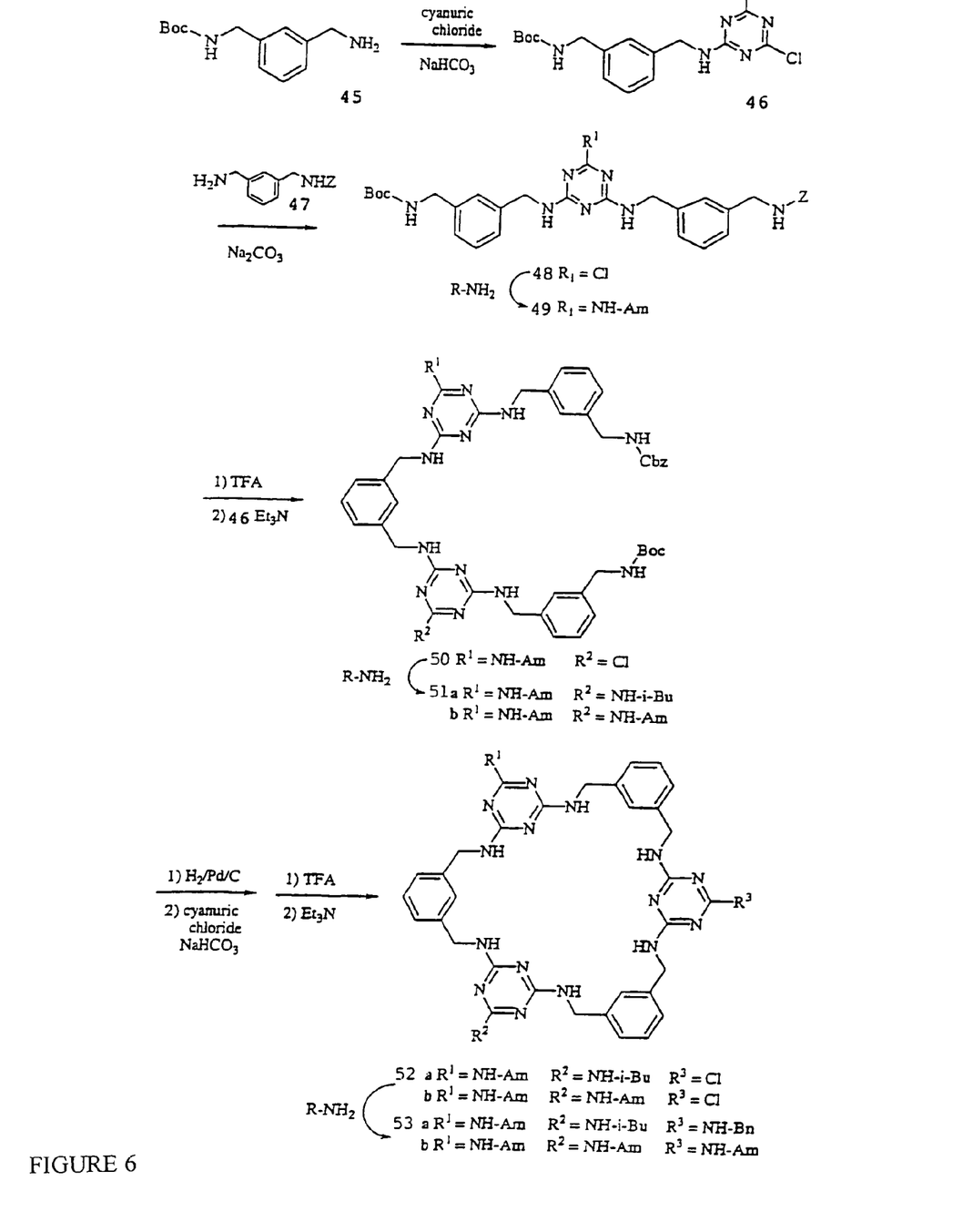
FIG. 6 shows a reaction scheme for preparing macrocyclic compounds of the present invention.

Preparation of Immobilised Macrocyclic Triazine Compounds by Solid Phase Synthesis Having shown that it is possible to synthesise macrocycles based on triazine-piperazine building blocks in solution, the next step was to repeat this or similar chemistry on a solid phase. Synthesising the macrocycles on a solid phase allows the possibility to generate many variants that may be screened easily for their binding properties. However, in order to attach the compounds to a resin, appropriate coupling chemistry or a 'handle' is required. A flexible way to achieve this without having to use Having shown that it is possible to synthesise macrocycles based on triazine-piperazine building blocks in solution, the next step was to repeat this or similar chemistry on a solid phase. Synthesising the macrocycles on a solid phase allows the possibility to generate many variants that may be screened easily for their binding properties. However, in order to attach the compounds to a resin, appropriate coupling chemistry or a 'handle' is required. A flexible way to achieve this without having to use one of the triazine rings was to use an additional functionality on one of the piperazine rings, as found in piperazine 30. It was also considered beneficial to have a linker between the resin and the triazine-piperazine based molecules, in order to permit detachment from the solid phase and analysis of their structure. This may be achieved by inserting a methionine residue between the piperazine 30 and the resin, in order to give a linkage that is stable to the conditions (acids, bases and nucleophiles) under which the macrocycles are synthesised. The methionine linkage may be subsequently cleaved with cyanogen bromide. Alternatives include a photocleavable bond or one involving a vicinal diol and cleavable by periodate oxidation. Furthermore, instead of building block 3, N-protected triazine-piperazine 32 was used, in which a trityl protective group is used such that it may be removed without cleaving a Boc group. Compound 32 is easily synthesised in the two steps shown in FIG. 5, in a 58% overall yield The solid phase synthesis was initiated by attachment of methionine and piperazine 30 using Fmoc chemistry and BOP as a coupling agent (FIG. 6). Cleavage using cyanogen bromide, after removal of the Fmoc and Boc groups and subsequent capping with $Ac_2O$, gave compound 35. Alternatively, removal of the Fmoc group and reaction with building block 32 gave bisubstituted triazine 36; the remaining chlorine was then substituted using an excess of isobutylamine. Removal of the Fmoc and Boo groups and subsequent capping with $Ac_2O$ or mesyl chloride, gave compounds 38 and 39 respectively.

The solid phase synthesis proceeded by selective removal of the trityl group, followed by a reaction with 32 which elongated the triazine-piperazine chain. The additional triazine was functionalised by a reaction with amyl amine. The synthesis was concluded by a reaction of the di-triazine with cyanuric chloride followed by ring closure and a final reaction with a third amine, after removal of the Boc group, to provide compound 44. In addition, a combinatorial library of 48 macrocyclic compounds was synthesised. Diversity was obtained by functionalisation of the triazines using various commercially available amines.

The solid phase synthesis is an efficient way to obtain a library of macrocycles that may act as receptor molecules towards a variety of complementary ligands.

EXAMPLE 3

Figure 7:
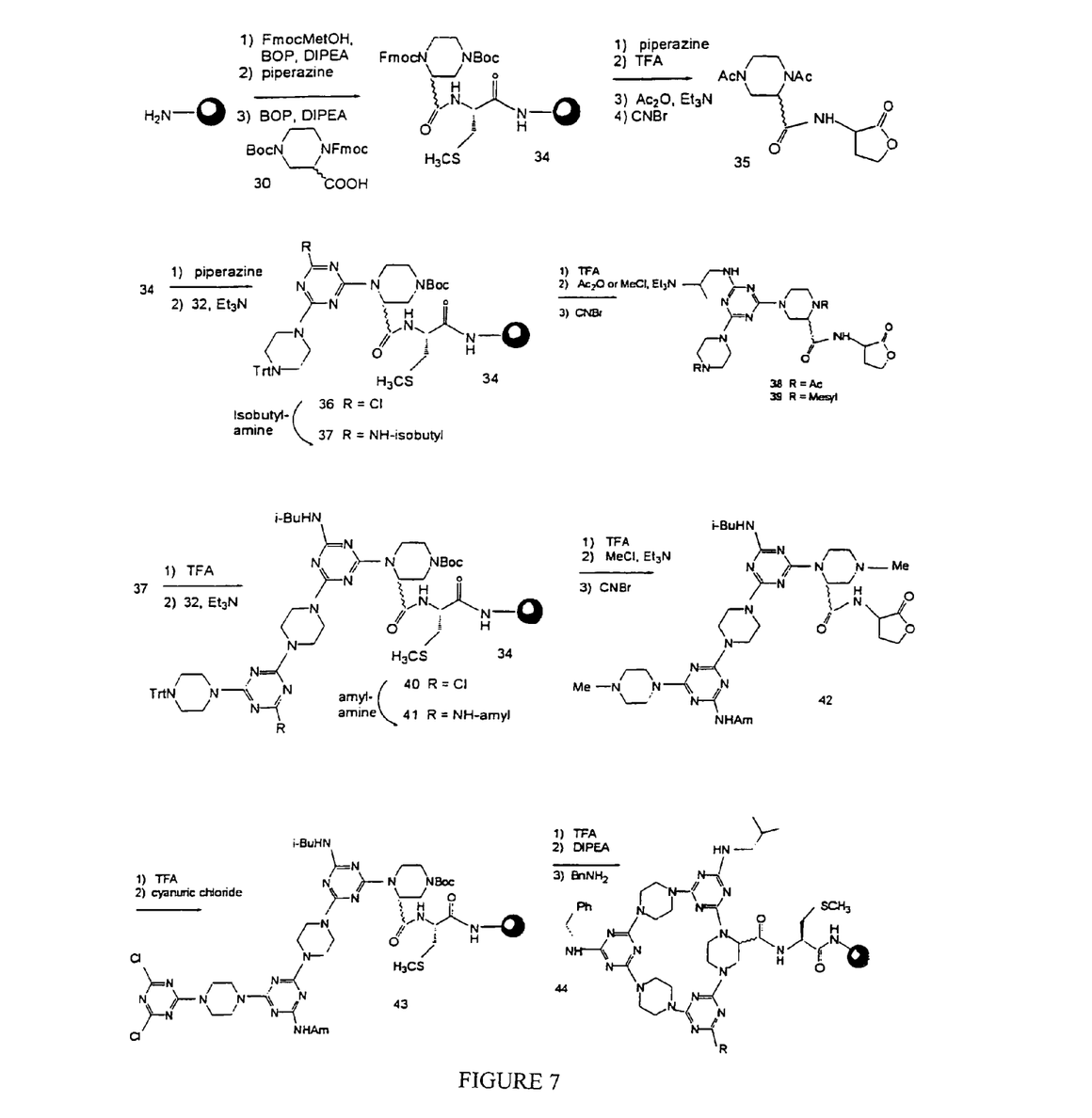
FIG. 7 shows a reaction scheme for preparing macrocyclic compounds of the present invention.

Preparation of Macrocyclic Compounds Incorporating Xylenediamine Spacer Groups To further exemplify the invention, other diamines such as xylencdiamine were used to create novel macrocyclic structures. For the preparation of such xylenediamine-triazine macrocycles, a new building block 46 was required and easily prepared from monoprotected xylenediamine 45 and cyanuric chloride in 85% yield, as illustrated in FIG. 7. After introduction of orthogonally protected linker 47(96% yield), the remaining chlorine in triazine 48 was substituted using an excess of amylamine to afford triazine 49 in 98% yield. Compound 49 can be regarded as a starting point for the preparation of xylene-triazine oligomers.

Monotriazine 49 was elongated by subsequent reactions with TFA and building block 46 to give bis-triazine 50 in 83% yield. Refluxing this compound with an excess of either amyl- or iso-butylamine afforded oligomers 51a and 51b both in 97% yield. In order to obtain precursors to macrocycles containing three triazine moieties, the Z-group from compounds 51 was removed and the resulting free amine was subsequently used in a reaction with cyanuric chloride. The crude dichlorotriazines obtained were used directly for cyclisation to afford macrocycles 52a and 52b. Yields of 36% and 34%, respectively were obtained for the cyclisation affording rings 52a and 52b. These lower yields are probably the result of the presence of rotamers, not all of which allow for cyclisation. The obtained macrocycles were further functionalised by refluxing in the presence of either amylamine or benzylamine to afford 53a and 53b in 71% and 72% yield respectively. The symmetric nature of 53b was reflected in its NMR spectrum, showing only one set of signals for the three amyl groups present. Furthermore, the macrocycles possess considerable conformational freedom. This leads to interconverting (on the NMR time scale) rotamers, as is evidenced by the broad signals for all hydrogens that sharpen upon heating from 25° to 50° C.

EXAMPLE 4

Binding of Cyanuric Acid to tris-(xylenediamine-triazine) Macrocycles

On the basis of molecular modelling studies, it was anticipated that compounds 53a and 53b should be able to completely encircle one molecule of cyanuric acid. To verify this expectation, compound 53b was titrated with 0.1 to 2 equivalents of cyanuric acid. After the addition of the appropriate amount of cyanuric acid, each sample was sonicated for three hours. Compound 53b was able to dissolve at least one equivalent of cyanuric acid in $CDCl_3$, which was otherwise poorly soluble in this solvent. The addition of cyanuric acid to compound 53b generates new signals in the NMR spectrum that were assigned to the newly-formed complex. The equilibrium established between the free and the bound state is slow on the NMR time scale, as both the free and bound state were visible. A binding constant of $2.5 \times 10^4$ $M^{-1}$ was calculated by non-linear regression of binding isotherms. The curve obtained was consistent with the postulated 1:1 stoichiometry.

Remarkably, the addition of cyanuric acid to 53a resulted in a second spot on TLC ($R_f$=0.85; 10% methanol in dichloromethane), moving faster than pure 53a ($R_f$=0.25). The spot for uncomplexed 53a completely disappeared after titrating the receptor with excess cyanuric acid, providing further evidence for the stability of the complex and the slow kinetics of the equilibrium. To test the selectivity of 53b towards cyanuric acid, attempts were made to bind analogues such as thymine, uracil and 5-bromouracil. However, none of these compounds were soluble in $CDCl_3$ in the presence of compound 53b indicating a lack of affinity for the macrocycle.

EXAMPLE 5

Binding of Octyl Glycosides to tris(xylenediamine-triazine) Macrocycles

There is circular presentation of hydrogen bond donors and acceptors in the macrocycles. This was examined further, by interaction with octyl glycosides. Preliminary molecular modelling studies suggested that the size of the ring is such that it could provide for hydrogen bond donors and acceptors complementary to those of pyranosides. Both compounds 53a and 53b were titrated with 1-O-n-octyl-α-D-glucopyranoside, 1-O-n-octyl-β-D-glucopyranoside and 1-O-n-octyl-β-D-galactopyranoside. In these experiments, the complexation-induced shift of the anomeric proton was observed, on increasing the number of equivalents of receptor molecule from 0.1 to 8. In all cases, an upfield complexation induced shift was observed for the anomeric proton of the glycosides, and all the binding isotherms matched well with the formation of 1:1 complexes. This was confirmed for all combinations by Job plots which had their maximum at a mole fraction of 0.5 for octyl-β-glucopyranoside and macrocycle 53b. Assuming 1:1 stoichiometry for these complexes, binding constants of $2.5-7.6 \times 10^3$ $M^{-1}$ were calculated using non-linear regression. Macrocycles 53a and 53b showed similar selectivities, both favouring octyl-β-glucopyranoside.

Specific reactions will now be described, in the following experimental section.

Reactions were carried out at ambient temperature unless stated otherwise. TLC analysis was performed on polyester pre-coated silicagel (250 mm, 5–17 mm) plates. Spots were visualised with UV light, ninhydrin (0.3 g in 100 mL HOAc/n-BuOH 3:97 v/v) or $Cl_2$-TDM. Column chromatography was performed on Merck kieselgel 60 (40–63 μm) and flash column chromatography on Merck kieselgel 60H (5–40 μm, applying 1 bar pressure). $^1H$ and $^{13}C$ NMR spectra were recorded with a Jeol Lambda 400 spectrometer (399.65 MHZ for $^1H$, chemical shift values are given in ppm relative to TMS; 100.4 MHZ for $^{13}C$, chemical shift values are given in ppm relative to $CDCl_3$ (δ=77.0 ppm) or [$D_6$] DMSO (δ=39.5 ppm)). The temperature was 298K (±0.5 K) for all experiments unless stated otherwise. Electron Spray Mass Spectrometry (ESI), Fast Atom Bombardment (FAB) and Liquid secondary Ion Mass Spectrometry (LSIMS) were carried out on a Bruker Bio-Apex II FT-ICR, Micromass Q-TOF or MSI Concept.

Compound 2

To a solution of 3.44 g piperazine (39.9 mmol) in 100 mL DCM, a solution of 4.37 g $Boc_2O$ (20.0 mmol) in 50 mL DCM was added over a period of three hours. The mixture was allowed to stir 22 hours before the solvent was evaporated. To the residue 100 mL water was added and the insoluble product was removed by filtration. The aqueous solution was extracted with three portions of 100 mL DCM and the combined organic layers were evaporated to afford 3.08 g Boc-piperazine (83%).

Compound 3

A fine slurry of cyanuric chloride was prepared by adding a solution of 1.11 g cyanuric chloride (6.0 mmol) in 24 mL acetone into 36 mL of well stirred ice-water. A solution of 1.12 g Compound 2 (6.0 mmol) in 10 mL acetone and 504 mg $NaHCO_3$ (6.00 mmol) in 10 mL water were added. After stirring the mixture for 2 hours at 0° C. the solid was filtered off, washed with water and dried in vacuo over $P_2O_5$ affording 1.93 g (96%) of product. $R_f$=0.63 (EtOAc/hexanes 1:1). HRMS (ESI) calcd for $C_{12}H_{17}Cl_2N_5NaO_2$ $(M+Na)^+$: 356.0657. found m/z: 356.0685.

Compound 4

To a solution of 559 mg Compound 2 (3.0 mmol) and 460 mL $Et_3N$ (3.3 mmol) in 20 mL DCM, a solution of 433 μL benzyl chloroformate (3.03 mmol) in 10 mL DCM was added at 0° C. The mixture was stirred at room temperature for 30 minutes before the solution was concentrated in vacuo. The residue was dissolved in EtOAc and the resulting solution was washed with 1M $KHSO_4$ (twice), 5% $NaHCO_3$, brine and dried on $Na_2SO_4$. Evaporation of the solvent yielded 957 mg of title compound (100%). $R_f$=0.55 (EtOAc/hexanes 1:1).

Compound 5

At 0° C. 10 mL of TFA was added to a solution of 4.14 g of Compound 4 (12.9 mmol) in 30 mL DCM. The mixture was stirred for 30 minutes at room temperature before it was concentrated in vacuo. To the residue 150 mL 1M NaOH was added and the aqueous layer was extracted with DCM (150 and 100 mL subsequently) and the combined organic layers were dried on $MgSO_4$ and evaporated to afford 2.85 g of 1-Z-piperazine (100%).

Compound 6

To a solution of 1.21 g Compound 5 (5.50 mmol) in 30 mL water, 583 mg $Na_2CO_3$ (5.50 mmol) and a suspension of 1.67 g Compound 3 (5.00 mmol) in 10 mL acetone were added. After stirring at 65° C. for 5 hours the white solid was filtered off and washed with water. Drying in vacuo over $P_2O_5$ overnight yielded 2.51 g of product (97%). $R_f$=0.25 (1% MeOH in DCM). HRMS (FAB) calcd for $C_{24}H_{33}ClN_7O_4$ $(M+H)^+$: 518.2283. found m/z: 518.2291.

Compound 7a

A solution of 1.04 g Compound 6 (2.0 mmol) and 1159 μL amylamine (10.0 mmol) in 20 mL THF was refluxed for 6 hours before the solvent was evaporated. The residue was dissolved in EtOAc and the resulting solution was washed with 1M $KHSO_4$ (twice), water, 5% $NaHCO_3$, brine and dried on $MgSO_4$. Evaporation of the solvent afforded 1.13 g of trisubstituted triazine (99%). $R_f$=0.08 (1% MeOH in DCM). HRMS (ESI) calcd for $C_{29}H_{45}N_8O_4$ $(M+H)^+$: 569.35582. found m/z: 569.3562.

Compound 7b

Compound 7b was prepared from Compound 6 (1.55 g, 3.0 mmol) and 2-phenylethylamine (1.88 mL, 15.0 mmol) according to the procedure described for Compound 7a, except that refluxing was for 24 hours. $R_f$=0.44 (EtOAc/hexanes 1:1). HRMS (ESI) calcd for $C_{32}H_{42}N_8O_4$ $(M+H)^+$: 603.3407. found m/z: 603.3409

Compound 9

To a solution of 989 mg Compound 7a (1.74 mmol) in 6 mL DCM, 2 mL TFA was added and the mixture was stirred for 30 minutes before it was evaporated. The residue was coevaporated with THF three times. The residue was redissolved in 30 mL THF and 485 μL $Et_3N$ (3.48 mmol) and 581 mg Compound 3 (1.74 mmol) were added. The mixture was stirred for 2 hours at 40° C. and kept basic by the addition of Et$_3$N before the volatiles were removed in vacuo. The residue was taken up in EtOAc and the resulting solution was washed with 1M KHSO$_4$ (twice), water, 5% NaHCO$_3$, brine and dried on MgSO$_4$. Evaporation of the solvent and column chromatography (eluent: EtOAc/hexanes 1:2) afforded 1.33 g of product (100%). R$_f$=0.51 (EtOAc/hexanes 1:1). HRMS (ESI) calcd for C$_{36}$H$_{53}$ClN$_{13}$O$_4$ (M+H)$^+$: 766.4032. found m/z: 766.4028.

Compound 10

Compound 10 was prepared from Compound 9 (1.16 g, 1.51 mmol) and isobutylamine (665 μL, 6.69 mmol) in 10 mL THF and refluxed overnight. The solvent was removed in vacuo and the residue was redissolved in EtOAc. The resulting solution was washed with 1M KHSO$_4$ (twice), water (twice), 5% NaHCO$_3$ and brine. Drying on MgSO$_4$ and evaporation of the solvent afforded 1.13 g of product (93%). R$_f$ 0.52 (EtOAc/Hexanes 1:1). HRMS (ESI) calcd for C$_{40}$H$_{63}$N$_{12}$O$_4$ (M+H)$^+$: 803.5151. found m/z: 803.5149.

Compound 11

To Compound 10(1.10 g, 1.37 mmol) in 25 mL THF/EtOH (4:3), 350 mg of Pd/C (10%) was added and the resulting solution was stirred under a hydrogen atmosphere overnight. The catalyst was filtered off and the filtrate evaporated. The residue was dissolved in 3 mL acetone and the resulting solution was added to a freshly prepared suspension of 111 mg cyanuric chloride (0.60 mmol), precipitated from 5 mL acetone in 5 mL water, after which 50 mg NaHCO$_3$ (0.60 mmol) was added. After stirring for two hours at 0° C. the aqueous suspension was extracted with DCM (twice) and the combined organic layers were dried on MgSO$_4$ and evaporated. Column chromatography (eluent: 2% MeOH in DCM) yielded 595 mg of product (61%). R$_f$=0.46 (EtOAc/hexanes 1:1). HRMS (ESI) calcd for C$_{35}$H$_{56}$Cl$_2$N$_{17}$O$_2$ (M+H)$^+$: 816.4180. found m/z: 816.4184.

Compound 12

Compound 12 was prepared from Compound 10 (0.40 g, 0.50 mmol) according to the procedure described for Compound 9. Column chromatography (eluent: EtOAc/hexanes 2:3) afforded 465 mg of product (93%). R$_f$ 0.45 (EtOAc/Hexanes 1:1). HRMS (ESI) calcd for C$_{47}$H$_{71}$ClN$_{19}$O$_4$ (M+H)$^+$: 1000.5625. found m/z: 1000.5649.

Compound 13

A solution of 0.42 g Compound 12 (0.42 mmol) and 239 μL cyclohexylamine (2.09 mmol) in 5 mL THF was refluxed for 20 hours. The solvent was removed in vacuo and the residue was redissolved in EtOAc. The resulting solution was washed with water (acidified to pH 2 with 1M HCl), water (twice), 5% NaHCO$_3$, brine, dried on MgSO$_4$ and evaporated, which afforded 413 mg of product (92%). R$_f$ 0.40 (EtOAc/Hexanes 1:1). HRMS (ESI) calcd for C$_{59}$H$_{82}$N$_{20}$NaO$_4$ (M+Na)$^+$: 1085.6726. found m/z: 1085.6744.

Compound 14

To a solution of 0.35 g Compound 13 (0.33 mmol) in 20 mL THF/EtOH (1:1), 200 mg of Pd/C (10%) was added and the resulting solution was stirred under a hydrogen atmosphere overnight. The catalyst was filtered off and the filtrate evaporated. The residue was dissolved in 2 mL acetone and the resulting solution was added to a freshly prepared suspension of 61 mg cyanuric chloride (0.33 mmol), precipitated from 4 mL acetone in 6 mL water, after which 28 mg NaHCO$_3$ (0.33 mmol) was added. After stirring for two hours at 0° C. the aqueous suspension was extracted with DCM (three times) and the combined organic layers were dried on MgSO$_4$ and evaporated. Column chromatography (eluent: EtOAc/hexanes 1:2) yielded 227 mg of the title compound (68%). R$_f$ 0.52 (EtOAc/hexanes 1:1). HRMS (ESI) calcd for C$_{48}$H$_{76}$Cl$_2$N$_{23}$O$_2$ (M+H)$^+$: 1076.5924. found m/z: 1076.5945.

Compound 15

To a solution of 0.36 g of Compound 13 (0.34 mmol) in 6 mL DCM, 2 mL TFA was added and the mixture was stirred for 30 minutes before it was evaporated. The residue was coevaporated with THF three times. The residue was redissolved in 10 mL THF and 95 μL Et$_3$N (0.68 mmol) and 0.11 g Compound 3 (0.34 mmol) were added. The mixture was stirred for 2 hours at 40° C. and kept basic by the addition of Et$_3$N before the volatiles were removed in vacuo. The residue was taken up in EtOAc and the resulting solution was washed with water (acidified to pH 2 with 1M HCl), water (twice), 5% NaHCO$_3$, brine and dried on MgSO$_4$. Evaporation of the solvent and column chromatography (eluent: EtOAc/hexanes 2:3) afforded 378 mg of product (88%). R$_f$ 0.45 (EtOAc/Hexanes 1:1). R$_f$ 0.42 (EtOAc/hexanes 1:1). HRMS (ESI) calcd for C$_{60}$H$_{90}$ClN$_{25}$NaO$_4$ (M+Na)$^+$: 1282.7194. found m/z: 1282.7246.

Compound 16

Compound 15 was functionalised (0.42 g, 0.33 mmol) according to the procedure described for Compound 12 except that cyclohexylamine was replaced by aniline and the reaction time was extended to 36 hours, to afford 410 mg of the title compound (93%). R$_f$ 0.38 (EtOAc/hexanes 1:1). HRMS (ESI) calcd for C$_{66}$H$_{97}$N$_{26}$O$_4$ (M+H)$^+$: 1317.8157. found m/z: 1317.8145.

Compound 17

Compound 17 was prepared from Compound 16 (0.13 g, 0.33 mmol) according to the procedure described for Compound 14, except that the reaction time was 9 hours, to yield 74 mg of compound 17 (56%). R$_f$ 0.47 (EtOAc/hexanes 1:1). HRMS (ESI) calcd for C$_{61}$H$_{90}$Cl$_2$N$_{29}$O$_2$ (M+H)$^+$: 1330.7204. found m/z: 1330.7208.

Compound 18

Compound 18 was prepared from Compound 16 (0.11 g, 84 mmol) according to the procedure described for Compound 15. Column chromatography (eluent: 2.5% MeOH in DCM) afforded 89 mg of the title compound (70%). R$_f$ 0.20 (2.5% MeOH in DCM).

Compound 19

Compound 19 was prepared from Compound 18 (0.24 g, 0.16 mmol) and 2-phenylethylamine (303 μL, 2.42 mmol) according to the procedure described for Compound 12, except that the reaction time was 5 hours, to yield 241 mg of product (94%). R$_f$ 0.17 (3% MeOH in DCM), 0.72 (EtOAc/hexanes 2:1). HRMS (ESI) calcd for C$_{81}$H$_{114}$N$_{32}$NaO$_4$ (M+Na)$^+$: 1621.9598. found m/z: 1621.9646.

Compound 20

Compound 20 was prepared from Compound 19 (0.14 g, 86 mmol) according to the procedure described for Compound 11, except that the reaction time was 17 hours. Column chromatography (eluent: 2.3% MeOH in DCM) afforded 104 mg of product (79%). R$_f$ 0.33 (3% MeOH in DCM). HRMS (ESI) calcd for C$_{76}$H$_{108}$Cl$_2$N$_{35}$O$_2$ (M+H)$^+$: 1612.8796. found m/z: 1612.8746.

Compound 22

A solution of 0.17 g Compound 11 (0.21 mmol) in 25 mL 4M HCl in dioxane was stirred for two hours. The volatiles were removed in vacuo and the residue was coevaporated with THF twice. The intermediate was dried in vacuo in a desiccator on KOH for one hour. Subsequently, the intermediate was dissolved in 75 mL DMF and to the resulting solution, a solution of 0.47 mL Et$_3$N (3.4 mmol) in 50 mL DMF was added dropwise at 45° C. After continuing stirring for 30 minutes at this temperature the solvent was removed in vacuo. The residue was dissolved in DCM and the resulting solution was washed with 1M HCl, water and dried on MgSO$_4$. Column chromatography (eluent: 3% MeOH in DCM) afforded 115 mg of Compound 22 (69%). R$_f$ 0.52 (3% MeOH in DCM). HRMS (ESI) calcd for C$_{30}$H$_{47}$ClN$_{17}$ (M+H)$^+$: 680.3883. found m/z: 680.3851.

Compound 23

A solution of 0.10 g Compound 12 (94 mmol) in 10 mL 4M HCl in dioxane was stirred for four hours. The volatiles were removed in vacuo and the residue was coevaporated with THF twice. The intermediate was dried in vacuo in a desiccator on KOH overnight. Subsequently, the intermediate was dissolved in 45 mL DMF and to the resulting solution, a solution of 0.13 mL Et$_3$N (0.94 mmol) in 5 mL DMF was added dropwise at 45° C. After continuing stirring for 30 minutes at this temperature the solvent was removed in vacuo. The residue was dissolved in DCM and the resulting solution was washed with water (twice), brine and dried on MgSO$_4$. Column chromatography (eluent: 3% MeOH in DCM) afforded a mixture of Compound 23 and its corresponding dimer. These were separated by gel permeation chromatography (eluent: DCM/MeOH 2:1) to afford 20 mg of Compound 23 (23%). R$_f$ 0.20 (3% MeOH in DCM). HRMS (LSIMS) calcd for C$_{43}$H$_{67}$ClN$_{23}$ (M+H)$^+$: 940.5633. found m/z: 940.5723.

Additionally, 27 mg dimer was isolated (31%): R$_f$ 0.17 (3% MeOH in DCM). HRMS (LSIMS) calcd for C$_{86}$H$_{133}$Cl$_2$N$_{46}$ (M+H)$^+$: 1880.1193. found m/Z: 1880.1048.

Compound 24

A solution of 72 mg Compound 17 (54 mmol) in 6 mL TFA/DCM 1:1 was stirred for one hour. The volatiles were removed in vacuo and the residue was coevaporated with THF twice. The intermediate was dried in vacuo in a desiccator on KOH overnight. Subsequently, the intermediate was dissolved in 10 mL DMF and to the resulting solution 75 µL Et$_3$N (0.54 mmol) was added dropwise at 45° C. After continuing stirring for 30 minutes at this temperature the solvent was removed in vacuo. The residue was dissolved in DCM and the resulting solution was washed with water (twice), brine and dried on MgSO$_4$. Column chromatography (eluent: 2.5% MeOH in DCM) afforded 38 mg of macrocyclic Compound 24 (59%). The crude product was used without further purification to prepare Compound 28. R$_f$ 0.32 (3% MeOH in DCM). HRMS (ESI) calcd for C$_{56}$H$_{81}$ClN$_{29}$ (M+H)$^+$: 1194.6918. found m/z: 1194.6938.

Compound 25

A solution of 0.10 g Compound 20 (64 mmol) in 6 mL TFA/DCM 1:1 was stirred for three hours. The volatiles were removed in vacuo and the residue was coevaporated with THF three times. The intermediate was dried in vacuo in a desiccator on KOH overnight. Subsequently, the intermediate was dissolved in 15 mL DMF and the resulting solution was added dropwise to a solution of 89 µL Et$_3$N (0.64 mmol) in 15 mL DMF at 45° C. Stirring was continued for 45 minutes at this temperature before the solvent was removed in vacuo. The residue was dissolved in DCM and the resulting solution was washed with water (twice) and brine. A precipitate formed in the aqueous layer, which was extracted with DCM until it disappeared. The combined organic layers were dried on MgSO$_4$ and evaporated. Column chromatography (eluent: 3% MeOH in DCM) afforded 78 mg of macrocycle 17 (83%). R$_f$ 0.57 (4% MeOH in DCM).

Compound 26

A solution of 0.13 g Compound 22 (0.19 mmol) and 204 mL benzylamine (1.87 mmol) in 4 mL THF was refluxed for 36 hours. The solvent was evaporated and the residue taken up in DCM. The resulting solution was washed with 1M HCl, water (three times), 5% NaHCO$_3$, dried on MgSO$_4$ and evaporated. Column chromatography (eluent: 4% MeOH in DCM) afforded 110 mg of Compound 22 (78%). R$_f$ 0.30 (4% MeOH in DCM). HRMS (ESI) calcd for C$_{37}$H$_{55}$N$_{18}$ (M+H)$^+$: 751.4852. found m/z: 751.4873.

Compound 27

A solution of 5.0 mg Compound 23 (5.3 µmol) and 20 µL benzylamine (0.16 mmol) in 1.5 mL THF was refluxed for 24 hours. The solvent was evaporated and the residue taken up in DCM. The resulting solution was washed with 1M HCl, water (twice), 5% NaHCO$_3$, brine, dried on MgSO$_4$ and evaporated. Column chromatography (eluent: 3% MeOH in DCM) afforded 4.0 mg of Compound 27 (74%). R$_f$ 0.46 (5% MeOH in DCM). HRMS (ESI) calcd for C$_{51}$H$_{76}$N$_{24}$ (M+H)$^+$: 1025.6763. found m/z: 1025.6696.

Compound 28

A solution of 35 mg Compound 24 (29 µmol) and 55 µL benzylamine (0.44 mmol) in 2 mL THF was refluxed for 6 hours. The solvent was removed in vacuo and the residue was redissolved in EtOAc. The resulting solution was washed with water (acidified to pH 4 with 1M HCl), water, 5% NaHCO$_3$, brine, dried on MgSO$_4$ and evaporated. Gel permeation chromatography (eluent: DCM/MeOH 2:1) afforded 30 mg of product (80%). R$_f$ 0.52 (4% MeOH in DCM). HRMS (LSIMS) calcd for C$_{64}$H$_{91}$N$_{30}$ (M+H)$^+$: 1279.8043. found m/z: 1279.8091.

Compound 29

A solution of 74 mg Compound 25 (50 µmol) and 82 µL benzylamine (0.75 mmol) in 3 mL THF was refluxed for 36 hours and stirred at room temperature overnight. The solvent was removed in vacuo and the residue was redissolved in DCM. The resulting solution was washed with water (acidified with 0.6 mL 1M HCl), water (three times), dried on MgSO$_4$ and evaporated. Column chromatography (eluent: 3.5% MeOH in DCM) followed by gel permeation chromatography (eluent: DCM/MeOH 2:1) afforded 57 mg of Compound 29 (74%). R$_f$0.37 (4% MeOH in DCM). HRMS (ESI) calcd for C$_{78}$H$_{107}$N$_{36}$ (M+H)$^+$: 1547.9474. found m/z: 1547.9496.

Compound 45

Compound 45 was synthesised according to published methods. The product was purified further by column chromatography (eluent: 30% MeOH in DCM). 11 mL xylenediamine and 2.18 g Boc$_2$O (10.0 mmol) afforded 1.69 g (72%) of title compound. Compound 46 Compound 46 was prepared from Compound 45 (1.59 g, 6.73 mmol) according to the procedure described for Compound 3, except that the reaction time was 3 hours, to afford 2.20 g of product (85%). R$_f$ 0.57 (EtOAc/hexanes 1:1).

Compound 47

Compound 47 was prepared from Compound 45 (1.57 g, 6.64 mmol) according to the procedures described for Compound 4 and Compound 5, to give 1.36 g product (94%). $R_f$ 0.18 (10% MeOH and 1% $Et_3N$ in DCM).

Compound 48

To a solution of 807 mg Compound 47 (2.99 mmol) in 20 mL water/acetone 1:1, 316 mg $Na_2CO_3$ (2.99 mmol) and a solution of 1.04 g monosubstituted triazine 20 (2.71 mmol) in 7 mL acetone were added. After stirring at 65° C. for 5 hours the suspension was cooled to room temperature and the white solid filtered off and washed with water. Drying in vacuo over $P_2O_5$ overnight yielded 1.60 g of product (96%). $R_f$ 0.64 (10% MeOH in DCM). HRMS (ESI) calcd for $C_{32}H_{36}ClN_7NaO_4$ $(M+Na)^+$: 640.2415. found m/z: 640.2446.

Compound 49

Compound 49 was prepared from Compound 48 (1.00 g, 1.62 mmol) according to the procedure described for Compound 7a, to afford 1.06 g of the title compound (98%). $R_f$ 0.66 (10% MeOH in DCM). HRMS (ESI) calcd for $C_{37}H_{49}N_8O_4$ $(M+H)^+$: 669.3877. found m/z: 669.3855.

Compound 50

Compound 50 was prepared from Compound 49 (1.03 g, 1.54 mmol) and Compound 26 (563 mg, 1.54 mmol) according to the procedure described for Compound 9, except that the reaction time was extended to 4 hours. Column chromatography (eluent: 4% MeOH in DCM) afforded 1.17 g of product (83%). $R_f$ 0.50 (10% MeOH in DCM). HRMS (ESI) calcd for $C_{48}H_{59}ClN_{13}O_4$ $(M+H)^+$: 916.4501. found m/z: 916.4511.

Compound 51a

Compound 51a was prepared from Compound 50 (0.50 g, 0.52 mmol) and isobutylamine (414 mL, 4.17 mmol) according to the procedure described for Compound 10, to afford 500 mg of the title compound (97%). $R_f$ 0.47 (10% MeOH in DCM). HRMS (LSIMS) calcd for $C_{52}H_{69}N_{14}O_4$ $(M+H)^+$: 953.5626. found m/z: 953.5637.

Compound 51b

Compound 51b was prepared from Compound 50 (0.54 g, 0.59 mmol) and amylamine (543 µL, 4.69 mmol) according to the procedure described for Compound 10, to afford 550 mg of the title compound (97%). $R_f$ 0.53 (10% MeOH in DCM). HRMS (ESI) calcd for $C_{53}H_{71}N_{14}O_4$ $(M+H)^+$: 967.5783. found m/z: 967.5748.

Compound 52a

To a solution of 0.24 g Compound 51a (0.25 mmol) in 14 mL THF/EtOH (1:1), 250 mg of Pd/C (10%) was added and the resulting solution was stirred under a hydrogen atmosphere overnight. After the addition of another 250 mg of Pd/C and stirring for 8 hours, the catalyst was filtered off and the filtrate evaporated. The residue was dissolved in 2 mL acetone and the resulting solution was added to a freshly prepared suspension of 44 mg cyanuric chloride (0.24 mmol), precipitated from 2 mL acetone in 4 mL water, after which 21 mg $NaHCO_3$ (0.25 mmol) was added. After stirring for 30 minutes at 0° C. the aqueous suspension was extracted with DCM and the organic layer was dried on $MgSO_4$ and evaporated. Flash column chromatography (eluent: 5% MeOH in DCM) yielded 106 mg of product (44%). The crude product was used directly to prepare macrocyclic Compound 52a. A solution of 55 mg precursor (57 µmol) in 5 mL 4M HCl in dioxane was stirred for six hours. The volatiles were removed in vacuo and the residue was coevaporated with THF twice. The intermediate was dried in vacuo in a desiccator on KOH overnight. Subsequently, the intermediate was dissolved in 25 mL DMF and, to the resulting solution, a solution of 79 µL DIPEA (0.57 mmol) in 5 mL DMF was added dropwise at 45° C. Another aliquot of DIPEA (79 µL) was added and stirring was continued for 45 minutes at 45° C. before the solvent was removed in vacuo. Flash column chromatography (eluent: 6% MeOH in DCM) afforded 17 mg of macrocycle Compound 52a (36%). The product was used without further purificaton to prepare macrocycle 53a. $R_f$ 0.25 (6% MeOH in DCM). HRMS (ESI) calcd for $C_{42}H_{52}ClN_{17}$ $(M+H)^+$: 830.4359. found: 830.4302.

Compound 52b

To a solution of 0.26 g Z-compound (0.27 mmol) in 14 mL THF/EtOH (1:1) 350 mg of Pd/C (10%) was added. After stirring the solution under a hydrogen atmosphere overnight, the catalyst was filtered off and the filtrate evaporated. The residue was dissolved in 2 mL acetone/THF (1:1) and the resulting solution was added to a freshly prepared suspension of 47 mg cyanuric chloride (0.26 mmol), precipitated from 2 mL acetone in 4 mL water, after which 23 mg $NaHCO_3$ (0.27 mmol) was added. After stirring for 30 minutes at 0° C., water was added, the aqueous suspension extracted with DCM and the combined organic layers were dried on $MgSO_4$ and evaporated. Flash column chromatography (eluent: 5% MeOH in DCM) yielded 127 mg of intermediate product (48%). The crude product was used directly to prepare macrocyclic Compound 52b according to the procedure described for Compound 52a. Flash column chromatography (eluent: 4.5% MeOH in DCM) afforded 37 mg of Compound 52b (34%). The product was used without further purification to prepare Compound 53b. $R_f$ 0.11 (5% MeOH in DCM). HRMS (ESI) calcd for $C_{43}H_{54}ClN_{17}$ $(M+H)^+$: 844.4509. found m/z: 844.4542.

Compound 53a

A solution of 17 mg Compound 52a (20 µmol) and 22 µL benzylamine (0.20 mmol) in 3 mL THF was refluxed overnight. The solvent was removed in vacuo and the residue was purified by column chromatography (eluent: 10% MeOH in DCM) followed by gel permeation chromatography (eluent: DCM/MeOH 2:1) to yield 13 mg of product (71%). $R_f$ 0.26 (10% MeOH in DCM). HRMS (ESI) calcd for $C_{49}H_{61}N_{18}$ $(M+H)^+$: 901.5327. found: 901.5374.

Compound 53b

A solution of 33 mg Compound 52b (39 µmol) and 43 µL amylamine (0.39 mmol) in 2 mL THF was refluxed for 20 hours. The solvent was removed in vacuo and the residue was purified by flash column chromatography (eluent: 7% MeOH in DCM) to afford 25 mg of product (72%). $R_f$ 0.22 (7% MeOH in DCM). HRMS (ESI) calcd for $C_{48}H_{67}N_{18}$ $(M+H)^+$: 895.5791. found m/z: 895.5864.

What is claimed is:

1. A macrocyclic compound of the formula wherein X is a triazine ring bearing an optionally-protected functional group or solid phase $R^1$; Y is a linker optionally bearing an optionally-protected functional group or solid phase $R^2$; m is at least 3, and each instance of Y, $R^1$ and $R^2$ may be the same or different.

2. The compound according to claim 1, wherein m is 3.

3. The compound according to claim 1, wherein Y includes a piperazine or xylene ring.

4. The compound according to claim 2, wherein Y includes a piperazine or xylene ring.

5. The compound according to claim 1, wherein $R^1$ or $R^2$ is a solid phase.

6. The compound according to claim 1, wherein $R^1$ is an optionally protected functional group.

7. A method for the capture of a target solute in a solution, comprising contacting the solution with a compound of claim 1, wherein $R^1$ and $R^2$ of said compound have affinity for the target solute.

8. A method for affinity binding of a target molecule, comprising contacting the target molecule with a compound of claim 1, wherein $R^1$ and $R^2$ of said compound have affinity for the target molecule.

* * * * *